US009981074B1

(12) United States Patent
Mills et al.

(10) Patent No.: US 9,981,074 B1
(45) Date of Patent: May 29, 2018

(54) METHOD FOR METALIZING NANOTUBES THROUGH ELECTROLYSIS

(71) Applicant: Louisiana Tech Research Corporation, Ruston, LA (US)

(72) Inventors: David Mills, Monroe, LA (US); Christen Boyer, Lafayette, LA (US)

(73) Assignee: Louisiana Tech Research Corporation, Ruston, LA (US)

( * ) Notice: Subject to any disclaimer, the term of this patent is extended or adjusted under 35 U.S.C. 154(b) by 0 days. days.

(21) Appl. No.: 15/274,704

(22) Filed: Sep. 23, 2016

Related U.S. Application Data

(60) Provisional application No. 62/232,507, filed on Sep. 25, 2015.

(51) Int. Cl.

| | |
|---|---|
| B82Y 30/00 | (2011.01) |
| A61L 31/12 | (2006.01) |
| A61L 31/04 | (2006.01) |
| A61L 31/08 | (2006.01) |
| A61L 31/16 | (2006.01) |
| C09C 1/42 | (2006.01) |
| C09C 3/06 | (2006.01) |
| C25D 3/46 | (2006.01) |
| C25D 3/48 | (2006.01) |
| C25D 3/50 | (2006.01) |
| C25D 3/38 | (2006.01) |

(52) U.S. Cl.
CPC ............. *A61L 31/128* (2013.01); *A61L 31/04* (2013.01); *A61L 31/088* (2013.01); *A61L 31/16* (2013.01); *B82Y 30/00* (2013.01); *C09C 1/42* (2013.01); *C09C 3/066* (2013.01); *C25D 3/38* (2013.01); *C25D 3/46* (2013.01); *C25D 3/48* (2013.01); *C25D 3/50* (2013.01); *A61L 2300/102* (2013.01); *A61L 2300/104* (2013.01); *A61L 2300/404* (2013.01); *A61L 2300/606* (2013.01); *A61L 2400/12* (2013.01); *C01P 2004/13* (2013.01); *C01P 2004/80* (2013.01)

(58) Field of Classification Search
CPC .................................................... B82Y 30/00
See application file for complete search history.

(56) References Cited

U.S. PATENT DOCUMENTS

| | | |
|---|---|---|
| 2007/0148457 A1 | 6/2007 | Wagner et al. |
| 2009/0092836 A1 | 4/2009 | Geckeler et al. |
| 2011/0174701 A1 | 7/2011 | Gallaway et al. |

FOREIGN PATENT DOCUMENTS

| | | |
|---|---|---|
| CN | 101999411 A | 4/2011 |
| CN | 101999414 A | 4/2011 |

OTHER PUBLICATIONS

Cavallaro et al, "Halloysite Nantubuies: Controlled Access and Release by Smart Gates", Nanomaterials, 2017, 7, 199.*
Rawtani, Deepak, and Y. K. Agrawal. "Multifarious applications of halloysite nanotubes: a review." Rev. Adv. Mater. Sci 30.3 (2012): 282-295.
Lvov, Yuri M., et al. "Halloysite clay nanotubes for controlled release of protective agents." Acs Nano 2.5 (2008): 814-820.
Vergaro, Viviana, et al. "Cytocompatibility and uptake of halloysite clay nanotubes." Biomacromolecules 11.3 (2010): 820-826.
Shchukin, Dmitry G., et al. "Halloysite nanotubes as biomimetic nanoreactors." Small 1.5 (2005): 510-513.
Abdullayev, Elshad, et al. "Halloysite tubes as nanocontainers for anticorrosion coating with benzotriazole." ACS applied materials & interfaces 1.7 (2009): 1437-1443.
Lvov, Yuri, and Elshad Abdullayev. "Functional polymer—clay nanotube composites with sustained release of chemical agents." Progress in Polymer Science 38.10 (2013): 1690-1719.
Karnik, Sonali, Kanesha Hines, and David K. Mills. "Nanoenhanced hydrogel system with sustained release capabilities." Journal of Biomedical Materials Research Part A 103.7 (2015): 2416-2426.
Karnik, Sonali, et al. "Performance evaluation of nanoclay enriched anti-microbial hydrogels for biomedical applications." Heliyon 2.2 (2016): e00072.
Sun, L., et al. "Drug coated clay nanoparticles for delivery of chemotherapeutics." Current Nanoscience 12 (2016): 1-8.
Wei, Wenbo, et al. "Enhanced efficiency of antiseptics with sustained release from clay nanotubes." RSC Advances 4.1 (2014): 488-494.
Sun, L., et al. "Polyelectrolyte coated clay nanotubes with pH controlled release." J. Nanomed Nannotechnol 2013 vol. 4, Issue 6, 1 page.
Karnik. S., et al."Nanoseeds: Nanoparticle Enhanced Hydrogels as Chemoattractants for Tissue Regeneration." TMJ Bioengineering Conference, Pittsburg, PA (Jun. 19-21, 2014).

(Continued)

*Primary Examiner* — Carlos A Azpuru
(74) *Attorney, Agent, or Firm* — Jones Walker LLP

(57) ABSTRACT

A method for forming metal nanoparticles on halloysite nanotubes. The method provides a water-based suspension solution containing about 0.002% to about 0.1% by weight of halloysite nanotubes. The suspension solution is maintained between about 2° C. and about 98° C. and under sufficient mixing that the nanotubes are maintained in substantially constant suspension. At least one positive and at least one negative metal electrode is positioned in the suspension solution, wherein the metal electrodes are at least 98% pure metal. A voltage is maintained across the electrodes of between about 10 and about 300 volts for a time sufficient to form metal ions on at least about 10% of a surface of the halloysite nanotubes.

19 Claims, No Drawings

(56) References Cited

OTHER PUBLICATIONS

Zhang, Yi, et al. "Palladium nanoparticles deposited on silanized halloysite nanotubes: synthesis, characterization and enhanced catalytic property." Scientific reports 3 (2013).
Chen, Sufang, et al. "Effect of preparation method on halloysite supported cobalt catalysts for Fischer-Tropsch synthesis." Journal of Natural Gas Chemistry 21.4 (2012): 426-430.
Liu, Peng, and Mingfei Zhao. "Silver nanoparticle supported on halloysite nanotubes catalyzed reduction of 4-nitrophenol (4-NP)." Applied Surface Science 255.7 (2009): 3989-3993.
Nicholson, James C., et al. "Dry Sintered Metal Coating of Halloysite Nanotubes." Applied Sciences 6.9 (2016): 265.
Cai, Zhen-Yu, et al. "Halloysite nanotubes supported gold catalyst for cyclohexene oxidation with molecular oxygen." Advances in Chemical Engineering and Science 1.01 (2011): 15.
Tang, Xuejiao, et al. "Halloysite-nanotubes supported FeNi alloy nanoparticles for catalytic decomposition of toxic phosphine gas into yellow phosphorus and hydrogen." Chemosphere 91.9 (2013): 1368-1373.
Rawtani, Deepak, Y. K. Agrawal, and Prajesh Prajapati. "Interaction Behavior of DNA with Halloysite Nanotube—Silver Nanoparticle-Based Composite." BioNanoScience 3.1 (2013): 73-78.
Pandey, G., et al. "Future Aspects of Halloysite Nanotubes in Forensic Investigations." Journal of Nanomedicine Research 2017. vol. 6, Issue 2, 2 pages.
D. K. Mills, and Karnik, S.. "Clay nanotubes as growth factor delivery vehicle for bone tissue formation." J. Nanomed Nanotechnot 4.6 (2013): 104.
Sun, Lin, and David K. Mills. "Halloysite nanotube-based drug delivery system for treating osteosarcoma." (In press, IEEE-Engineering in Biology andMedicine conference proceedings)(2014).

\* cited by examiner

METHOD FOR METALIZING NANOTUBES THROUGH ELECTROLYSIS

CROSS-REFERENCE TO RELATED APPLICATION

The application claims the benefit under 35 USC 119(e) of U.S. Provisional Application Ser. No. 62/232,507, filed Sep. 25, 2015, which is incorporated by reference herein in its entirety.

BACKGROUND OF INVENTION

Rubber polymers are used in the treatment of millions of patients each day. Bacterial and protein adherence to polymer materials, implanted or inserted into the body, are an early step in blood clots and biofilm formation, and typically result in infections, complications from the resultant infections, longer hospital stays, and perhaps death. Due to protein adsorption and subsequent bacterial adherence, biofilms are formed at interfaces between solid substrates and liquids. The prevention of bacterial and protein adherence and biofilm development on biomedical materials continues to be a major challenge in healthcare. Catheter-associated urinary tract infections (CAUTI) alone are the most common health-care-associated infection worldwide. Accordingly, there exists a significant need for new anti-infective medical grade polymer biomaterials.

DETAILED DESCRIPTION OF SELECTED EMBODIMENTS

One embodiment of the present invention is an antimicrobial/antifouling medical device. The "medical device" could be any device which implanted into, inserted into, or contacted with a human body (or other animal bodies in veterinary applications) in a manner which involves that risk of infection or other medical complication. Nonlimiting example of medical devices include catheters, and stents.

The medical device will typically be formed completely of a polymer matrix or at least be partially or wholly covered by (i.e., have an outer surfaced formed by) a polymer matrix. In general terms, the polymer matrix can be one of a of a plastic, a thermoplastic, a natural or synthetic rubber, a silicone, or a hydrogel.

Thermoplastics are normally formed from polymer resins that can be reheated, reshaped, and frozen repeatedly. Exemplary thermoplastics include acrylic, crylonitrile butadiene styrene (ABS), polylactic acid (PLA), celluloid, polyurethane, polypropylene, polycarbonate, and acrylic.

Natural rubbers generally mean polymers of the organic compound isoprene with minor impurities of other organic compounds. Synthetic rubbers generally mean rubber is made by the polymerization of a variety of petroleum-based precursors, with a prevalent example being styrene-butadiene rubbers (SBR).

In some embodiments, the polymer matrix may be of the type where the matrix itself has antifouling characteristics. In other embodiments, the polymer matrix will include an additive which provides the antifouling characteristic. Antifouling additives may include enzymes, polyelectrolytes, and chemicals that increase hydrophobicity such as fluoropolymer additives' including polytetrafluoroethylene (PTFE), fluorinated ethylene propylene and polyvinylidene fluoride (PVDF).

In many embodiments of the invention, any of the polymer matrices described above may include aluminosilicate nanotubes adhered on or in the polymer matrix surface, where the nanotubes have at least one antimicrobial transition metal formed on at least 10% of their outer surface. The nanotubes have a wide range of dimensions, but one example would be nanotubes having (i) an inner diameter of between about 15 and about 50 nanometers, (iI) an inner diameter of between about 30 and about 60 nanometers, and (iii) a length of between about 100 and about 2000 nanometers. Naturally occurring halloysite clays are one source for nanotubes in these size ranges. In preferred embodiments, the antimicrobial transition metal is at least one from the group consisting of silver, copper, gold, platinum, iron, nickel, titanium, and palladium.

In certain embodiments, the nanotubes are absorbed into the surface of the polymer matrix material. One method of absorbing the nanotubes into the polymer matrix is by a solvent swelling/deswelling method where the polymer matrix material is exposed to a solvent. Using this solvent swelling/deswelling method, sufficient nanotubes will be embedded in the polymer matrix that the nanotubes form at least at least 1% by weight of the polymer matrix forming the medical device.

In other embodiments, the nanotubes may be an additive mixed into the polymer as the (medical) device is formed, i.e., the nanotubes are mores/less evenly distributed throughout the polymer matrix structure as opposed to be absorbed onto the outer surface.

In certain embodiments of the present invention, a therapeutic agent may be releasably bound to the nanotubes. Therapeutic agents could include antibiotics, anti-cancer drugs, antibodies, or magnetic nanoparticles. On example of a therapeutic agent releasably bound to a nanotube is where the agent is temporarily adhered to the out surface of the nanotube and then the agent releases when environmental conditions change.

In another example, a therapeutic agent releasably bound to a nanotube when it is loaded into the lumen of the nanotube. The agent is initially loaded into the lumen and then, over time, the therapeutic agent escapes from the lumen.

The metalized nanotubes used in the polymer matrixes described above could manufactured by many conventional or future developed techniques. However, one preferred method for producing metalized nanotubes is through an electroplating process, i.e. a process of coating the surfaces of a metal object with a layer of a different metal through electrochemical means, usually to exploit different properties of the materials. The initial step in this process is creating a water-based suspension solution containing about 0.002% to about 0.1% by weight of halloysite nanotubes. As used herein, a water-based solution is formed of at least 50% water, and more commonly at least 95% water, but could be a solution that is anywhere between 50% and 99.99% water. Additives to the water-based suspension solution, in order to enhance electrodeposition or provide other process benefits, could include polyvinylpyrrolidone (PVP) or poly(vinyl alcohol) (PVP or PVOH(PVA)) which act to stabilize metal particles long term in solution. PVP, also commonly called polyvidone or povidone, is a water-soluble polymer made from the monomer N-vinylpyrrolidone. PVA is a water-soluble synthetic polymer and has the idealized formula $[CH2CH(OH)]_n$. For specific applications where it is desired to form metal salt compounds on the nanotubes, adding electrolytes/salts to the solution during the process will create the desired metal-salts. Likewise, other embodiments could add reducing agents for oxides and hydroxides, or metal deactivators/stabilizers, or surfactants to the solution.

Halloysite nanotubes will be then be suspended in the water-based solution. "Halloysite nanotube" includes any naturally-occurring or synthetic aluminosilicate tubular structure with a length of less than 100 microns and a diameter of less than 1 micron. As described above, the nanotubes have a wide range of dimensions, but one example would be nanotubes having (i) an inner diameter of between about 15 and about 50 nanometers, (ii) an outer diameter of between about 30 and about 60 nanometers, and (iii) a length of between about 100 and about 2000 nanometers. Naturally occurring halloysite clays are one source for nanotubes in these size ranges. The concentration of nanotubes can vary from 0.001% to 1% (or any subrange in between) by weight of nanotubes to suspension solution. A more preferred concentration range is about 0.002% to about 0.1% by weight, and most preferred is about 0.001% to about 0.01% by weight.

During the described method, the suspension solution is maintained between about 2° C. and about 98° C. (or any subrange in between) and under substantially constant mixing. One preferred temperature range is between about 40° C. and about 85° C. The suspension solution being under substantially constant mixing means a majority of particles that would eventually settle out under quiescent conditions are kept suspended in the fluid by mixing at least at intervals and with enough energy to maintain the suspended state. Stated in another manner, the solution is subject to sufficient mixing that most of the nanotubes are maintained in substantially constant suspension.

As a further step in the method, at least one positive and at least one negative metal electrode is positioned in the suspension solution. The position of the electrodes in the solution is not of significance and naturally different numbers of positive and negative electrodes could be positioned in the solution. In one embodiment, the metal electrodes are at least 98% pure metal, and more preferably, at least 99.99% pure metal, but could be any degree of purity between 95% and 99.999%. In preferred embodiments, the metal forming the electrode is a "transition metal," i.e., any element in the d-block of the periodic table, which includes groups 3 to 12 on the periodic table. In certain preferred embodiments, the transition metal is one from the group of silver, copper, gold, platinum, iron, nickel, titanium, or palladium. The electrodes could be the same metal or different metals. In one example, the cell might consist of two pieces of metal, one zinc and the other copper, each immersed each in a solution containing a dissolved salt of the corresponding metal. The two solutions are separated by a porous barrier that prevents them from rapidly mixing but allows ions to diffuse through.

Another step in the method is maintaining a voltage across the electrodes of between about 10 and about 300 volts for a time sufficient to form metal ions on at least about 10% of the surface of the halloysite nanotubes. As the process continues, the ions will form metal nanoparticles on the halloysite surface. In more preferred embodiments, a direct current will be supplied to the electrodes and the voltage will be maintained at a voltage anywhere between about 0.5 to about 240 volts. The voltage level will depend on the size of the electrodes and other factors as understood by those skilled in the art. The approximate time at this voltage to deposit metal over about 10% of the nanotubes' surfaces is about 30 minutes. In more preferred embodiments, the nanotubes will have metal deposited over about 50% to about 100% of their surface and this will require about 120 minutes.

In many embodiments, the method will include a drying step in order to place the metalized nanotubes in a more concentrated and convenient condition for further use. In one example, the metalized halloysite nanotubes are de-watered to a water content of less than about 1%, and more preferably, a water content of less than 0.001%. In another example, the drying step includes centrifuging the suspension solution, decanting a resulting water supernatant, and heat drying the supernatant.

The physical structure of metal particles electroplated on the halloysite surface, the binding process, reactivity of coated the halloysite, and the material property of the final construct is different from current fabrication methods for the metallization of the halloysite surface. For example, in production of copper-coated HNTs different particle sizes and elemental composition of material is produced.

Most prior fabrication methods use a multi-step method, a metal-salt mixture method and reducing agents, high temperatures, expensive equipment and often produce noxious reactants as a by-product of production. The later are harmful or toxic compounds that require proper disposal. The method disclosed herein for the fabrication of MHNTs is through the process of electrolysis. Metals nanoparticles, such as silver, copper, gold and other metal nanoparticles, can be directly deposited onto the (halloysite nanotube HNT) surface through this rapid low-cost method that is efficient, does not require expensive equipment, and does not produce unwanted waste products.

The invention claimed is:

1. A method for forming metal nanoparticles on halloysite nanotubes, the method comprising of the steps of:
   a. providing a water-based suspension solution containing about 0.002% to about 0.1% by weight of halloysite nanotubes;
   b. maintaining the suspension solution between about 2° C. and about 98° C. and sufficient mixing that the nanotubes are maintained in substantially constant suspension;
   c. positioning at least one positive and at least one negative metal electrode in the suspension solution, wherein the metal electrodes are at least 98% pure metal; and
   d. maintaining a voltage across the electrodes of between about 10 and about 300 volts for a time sufficient to form metal ions on at least about 10% of a surface of the halloysite nanotubes.

2. The method of claim 1, further comprising the step of de-watering the halloysite nanotubes to a water content of less than about 1%.

3. The method of claim 2, wherein the drying step comprises centrifuging the suspension solution, decanting a resulting water supernatant, and heat drying the supernatant.

4. The method of claim 3, wherein the metal is at least one from the group consisting of silver, copper, gold, platinum, iron, nickel, titanium, and palladium.

5. The method of claim 4, wherein the metal electrode is at least 99.99% pure metal.

6. The method of claim 1, wherein a direct current is supplied to the electrodes.

7. The method of claim 1, wherein the suspension solution is maintained between about 40° C. and about 85° C.

8. The method of claim 1, wherein the voltage across the electrodes is maintained for a time sufficient to form metal ions on at least about 50% of a surface of the halloysite nanotubes.

9. The method of claim 4, further comprising at least two positive or at least two negative electrodes, wherein the at least two electrodes are formed of different metals from the group consisting of silver, copper, gold, platinum, iron, nickel, titanium, and palladium.

10. The method of claim 1, further comprising the step of binding a therapeutic agent to the nanotubes.

11. The method of claim 10, wherein a therapeutic agent is loaded within a lumen of the nanotubes.

12. The method of claim 1, wherein the water-based suspension further includes water-soluble polymer.

13. The method of claim 1, wherein the nanotubes have an outer diameter of between about 30 and about 60 nanometers and a length of between about 100 and about 2000 nanometers.

14. A method for forming metal nanoparticles on halloysite nanotubes, the method comprising of the steps of:
 a. providing a water-based suspension solution containing at least about 0.002% by weight of halloysite nanotubes;
 b. maintaining the suspension solution between about 2° C. and about 98° C. and sufficient mixing that the nanotubes are maintained in substantially constant suspension;
 c. positioning at least one positive and at least one negative metal electrode in the suspension solution, wherein the metal electrodes are at least 98% pure metal; and
 d. maintaining a voltage across the electrodes of between about 10 and about 300 volts for a time sufficient to form metal ions on at least about 10% of a surface of the halloysite nanotubes.

15. The method of claim 14, further comprising the step of de-watering the halloysite nanotubes to a water content of less than about 1%.

16. The method of claim 14, wherein the metal is at least one from the group consisting of silver, copper, gold, platinum, iron, nickel, titanium, and palladium.

17. The method of claim 14, wherein a direct current is supplied to the electrodes.

18. The method of claim 16, wherein the voltage across the electrodes is maintained for a time sufficient to form metal ions on at least about 50% of a surface of the halloysite nanotubes.

19. The method of claim 18, wherein the suspension solution is maintained between about 40° C. and about 85° C.

* * * * *